United States Patent
Claude et al.

(10) Patent No.: US 7,201,935 B1
(45) Date of Patent: Apr. 10, 2007

(54) PLASMA-GENERATED COATINGS FOR MEDICAL DEVICES AND METHODS FOR FABRICATING THEREOF

(75) Inventors: Charles D. Claude, Sunnyvale, CA (US); Syed F. A. Hossainy, Fremont, CA (US); Shamim M Malik, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 667 days.

(21) Appl. No.: 10/245,530

(22) Filed: Sep. 17, 2002

(51) Int. Cl.
B05D 3/06 (2006.01)

(52) U.S. Cl. ............ 427/2.1; 427/2.24; 427/487; 427/488; 427/490; 427/407.1

(58) Field of Classification Search ............ 427/2.1, 427/2.24, 487–488, 490, 407.1
See application file for complete search history.

(56) References Cited

U.S. PATENT DOCUMENTS

| | | | |
|---|---|---|---|
| 4,977,901 A | 12/1990 | Ofstead | 128/772 |
| 4,994,298 A | 2/1991 | Yasuda | 427/41 |
| 5,112,457 A | 5/1992 | Marchant | 204/165 |
| 5,328,471 A | 7/1994 | Slepian | 604/101 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |

(Continued)

FOREIGN PATENT DOCUMENTS

EP   0 665 023   8/1995

(Continued)

OTHER PUBLICATIONS

Arefi et al., *Surface Treatment of Polymer Films by a Non Equilibrium Plasma*, J. Appl. Polymer Sci., 46:33-60 (1990).

Primary Examiner—Erma Cameron
(74) Attorney, Agent, or Firm—Squire, Sanders & Dempsey L.L.P.

(57) ABSTRACT

Coatings for implantable medical devices, such as stents, and methods of coating the devices are disclosed. The method includes forming a coating by plasma polymerization of a monomer or a blend of monomers.

12 Claims, 1 Drawing Sheet

U.S. PATENT DOCUMENTS

| | | | |
|---|---|---|---|
| 6,099,562 A | 8/2000 | Ding et al. | 623/1.46 |
| 6,110,188 A | 8/2000 | Narciso, Jr. | 606/153 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,335,029 B1 | 1/2002 | Kamath et al. | 424/423 |
| 6,613,432 B2 * | 9/2003 | Zamora et al. | 428/409 |
| 6,670,297 B1 * | 12/2003 | Brookhart et al. | 502/103 |

FOREIGN PATENT DOCUMENTS

| | | |
|---|---|---|
| EP | 0 970 711 | 1/2000 |
| WO | WO 00/12147 | 3/2000 |
| WO | WO 00/64506 | 11/2000 |
| WO | WO 01/01890 | 1/2001 |

* cited by examiner

FIG. 1

PLASMA-GENERATED COATINGS FOR MEDICAL DEVICES AND METHODS FOR FABRICATING THEREOF

BACKGROUND OF THE INVENTION

1. Field of the Invention

This invention relates to coatings for implantable medical devices, such as stents, and methods for coating the devices.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Stents are used not only for mechanical intervention but also as vehicles for providing biological therapy.

Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One conventional method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

One of the drawbacks and disadvantages associated with the use of such stents has been the relatively rapid depletion of the therapeutic substance from the polymer when the stent is subjected to body fluids. One way to control the rapid rate of release of the therapeutic substance from the coating is by using a topcoat membrane. A topcoat membrane serves as a barrier, retarding the diffusion of the therapeutic substance into the bloodstream.

The present invention discloses various topcoat layers and methods of fabricating the same.

SUMMARY

In accordance with one embodiment of the invention, a method of forming a coating for an implantable medical device is provided, the method comprises exposing the device to a plasma-polymerizable monomer or a blend of monomers in a gaseous form, the monomer or the blend being maintained at an initial pressure, initiating a plasma to cause the polymerization of the monomer or the blend to form a bulk layer of the coating, and changing the initial pressure of the monomer or the blend to a final pressure while maintaining the plasma to form a surface layer of the coating, wherein the bulk layer and the surface layer of the coating comprise different polymers. The plasma-polymerizable monomer can be vinylidene fluoride.

In accordance with another embodiment of the invention, a stent comprising a coating is provided, the coating includes a first layer having a therapeutic substance incorporated therein, and a second layer disposed over the first layer, the second layer including a first region formed by plasma polymerization of a monomer or a blend of monomers at a first pressure and a second region formed by plasma polymerization of a monomer or a blend of monomers at a second pressure different from the first pressure.

BRIEF DESCRIPTION OF THE DRAWINGS

The features and advantages of the embodiments of the present invention will become better understood with regard to the following description, appended claims, and accompanying drawings where:

DETAILED DESCRIPTION

The embodiments of this invention provide for rate-controlling topcoat membranes and methods of making such membranes for implantable medical devices, such as stents. The embodiments include two-polymer topcoat membranes as discussed below. The membranes can be optionally further modified to improve adhesion and/or to impart beneficial biological properties to the membrane.

According to the basic embodiment of the present invention, the stent can be pre-coated with a suitable polymer capable of being activated. The coating may optionally contain a therapeutic substance or an active agent, thus serving as a drug reservoir. One example of the suitable polymer is poly(ethylene-co-vinyl alcohol), known under the trade name "EVAL" available from EVAL Company of America of Lisle, Ill. EVAL has the general formula —[$CH_2$—$CH_2$]$_m$—[$CH_2$—$CH(OH)$]$_n$— and is a product of hydrolysis of ethylene-vinyl acetate copolymers. EVAL may also be a terpolymer and may include up to, for example, 5% (molar) units derived from styrene, propylene and other suitable unsaturated monomers. EVAL can be dissolved in a suitable solvent such as dimethylacetamide or dimethylsulfoxide and the solution can be applied onto the stent surface or onto a primer layer disposed on the stent surface by any common method such as spraying or dipping.

Alternatively, the stent can be pre-coated with fully or partially fluorinated polymers, one example of which includes poly(tetrafluoro ethylene) (PTFE) having the general formula —[$CF_2$—$CF_2$]$_n$—.

The coated stent can then be modified by depositing polymers onto the coated stent. The polymers are deposited by plasma polymerization. The process of modification of the pre-coated stent comprises the following steps:

(1) the surface of the coating is plasma-activated with argon;

(2) the plasma-activated coating is then exposed to a polymerizable monomer introduced into the plasma chamber in a gaseous form at a certain pressure;

(3) the plasma is re-initiated to cause polymerization of the monomer gas on the activated surface of the coating to form a bulk sub-layer of the polymeric topcoat membrane;

(4) the pressure in the plasma chamber is lowered while the same monomer in the gaseous form is continuously supplied into the chamber and while the plasma is maintained.

As a result, the topcoat membrane is obtained, the membrane having two sub-layers: a bulk sub-layer and a surface sub-layer. The polymer forming the surface sub-layer fabricated in step (4) can be different from the polymer forming the bulk of the membrane fabricated in step (3).

To activate the stent surface, the stent can be placed in a plasma chamber, and, in order to remove oxygenated species, the plasma chamber can then be evacuated to reach a pressure of less than about 5 mTorr. The chamber can then be purged with argon flowing at a rate of about 250 sccm, and a plasma, typically, argon or argon/oxygen plasma, can be initiated. Time needed for plasma activation can be between about 2 and 5 minutes, for example 3 minutes. A radio frequency (RF) energy source described below is used to generate plasma. After about 3 minutes, the RF power is terminated and the chamber pressure is reduced to below about 1 mtorr.

Process parameters for the argon plasma that can be employed are listed in Table 1 below.

TABLE 1

The Parameters of the Argon Plasma for Activation of the Surface of the Coating (>99.9% by Volume of Argon)

| Parameter | Parameter Range | Exemplary Value |
| --- | --- | --- |
| Gas flow rate (sccm) | 10 to 500 | 100 |
| Volume of chamber (cm³) | — | 2,000 |
| Pressure (mTorr) | 0.1 to 500 | 230 |
| RF power (Watts) | 100 to 500 | 100 |
| RF frequency (MHz) | 0.2 to 2,800 | 13.56 |
| Bias voltage--stent (kV) | 0 to −30 | 0 |
| Pulse width--stent (μs) | 7 to 20 | 20 |
| Frequency--stent (Hz) | DC - 2,000 | 100 |
| Bias voltage--grid (kV) | 0 to −30 | 0 |

If the argon/oxygen plasma is used for activation of the stent surface, the surface of the coating can be activated in a Plasma Ion Implantation Unit (PIIU). PIIU is an apparatus known to those having ordinary skill in the art. Process parameters for the argon/oxygen plasma that can be employed are listed in Table 2 below.

TABLE 2

The Parameters of the Argon/Oxygen Plasma for Activation of the Surface of the Coating (A Blend of 80% Argon and 20% Oxygen by Volume)

| Parameter | Parameter Range |
| --- | --- |
| Gas flow rate (sccm) | 60 to 200 |
| Volume of the PIIU chamber (cm³) | 2,000 |
| Pressure (mTorr) | 0.1 to 500 |
| RF power (Watts) | 5 to 100 |
| RF frequency (MHz) | 0.2 to 2,800 |
| Bias voltage--stent (kV) | −5 to −30 |
| Pulse width--stent (μs) | 7 to 20 |
| Frequency--stent (Hz) | DC - 2000 |
| Bias voltage--grid of the PIIU (kV) | −5 to −30 |

Following the process of activation described above, a polymerizable monomer gas is introduced into the plasma chamber, and the RF field is re-applied to induce polymerization of the monomer on the plasma-activated surface.

One example of a polymerizable monomer that can be used for making the bulk of the topcoat membrane is vinylidene fluoride (VDF) having the formula $CH_2=CF_2$. It is known that under plasma conditions, a multi-step process occurs, whereby VDF fragments into methylene radicals ($:CH_2$) and difluoromethylene radicals ($:CF_2$) and decomposition and decomposition/recombination thereof. Among possible paths of such recombination is a reaction between only the methylene radical species (reaction I) or a reaction between one methylene radical and one difluoromethylene radical species (reaction II):

where "n" and "m" are integers.

The process of polymerization predominantly follows reaction path (I) at lower pressures (less than about 30 mTorr, for instance, about 20 mTorr) leading to formation of mostly poly(ethylene) (PE)-like polymer. At higher pressures (above about 80 mTorr, for example, about 90 mTorr), due to the formation of difluoromethylene radical species, reaction (II) predominantly occurs, where recombination takes place equally between fluorinated and protonated methylene species. As a result, at higher pressures mostly a poly(vinylidene fluoride)(PVDF)-like polymer is obtained.

Figure 1:
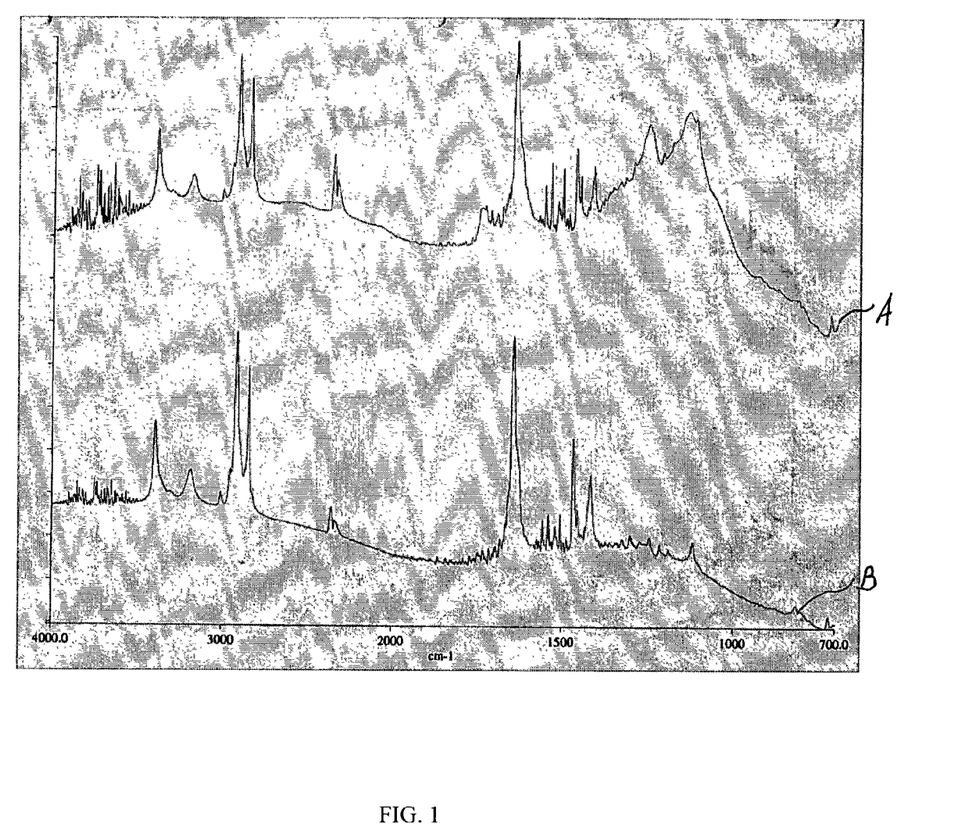
FIG. 1 shows infra-red spectra of products of plasma polymerization of vinylidene fluoride.

These experimental results are corroborated by infra-red spectra of the polymers formed as a result of plasma polymerization of VDF on a pre-coated stent (FIG. 1). The polymer obtained when the VDF pressure was 90 mTorr is shown by spectrum (A), and when the VDF pressure was 30 mTorr—by spectrum (B).

Comparing the two spectra side-by-side, one can clearly see that all the peaks corresponding to absorption of the C—H and C—C bonds are identical on both spectra. One can easily observe strong peaks at frequencies 2844 cm$^{-1}$ (symmetric vibrations), 2915 cm$^{-1}$ (asymmetric vibrations), in the 1450–1550 cm$^{-1}$ area (deformation vibrations) and in 1600–1700 cm$^{-1}$ area (inclusion of carbonyl species due to quenching of radicals with atmospheric oxygen). However, spectrum (A) also shows peaks at 1254 cm$^{-1}$ and 1140 cm$^{-1}$, which are absent on spectrum (B). These peaks characterize absorption of the C—F bonds. Therefore, at lower pressure a PE-like polymer, rather than a PVDF-like polymer, is predominantly formed.

Thus, if it is desirable that the material forming bulk of the topcoat membrane be PVDF-like polymer, plasma polymerization is conducted at the pressure of VDF of about 90 mTorr or more. If the formation of PE-like material in the surface sub-layer of the topcoat membrane is needed, plasma polymerization is conducted at the lower VDF pressure of about 30 mTorr or less.

Polymerizable monomers other than VDF can be used in the alternative. Examples of such monomers include blends of alkenes and fluoroalkenes where the blends comprise at least one monomer of Group 1 and at least one monomer of Group 2.

Monomers of Group 1 can be alkanes, alkenes, di- or multifunctional alcohols, and their derivatives. Examples of suitable monomers of Group 1 include methane, ethane, dimethoxyethane, ethylene, propylene, ethylene glycol, or glycerol.

Monomers of Group 2 can be fluorinated alkanes, fluorinated alkenes, and their derivatives, for example, 1,2-difluoroethane, tetrafluoroethylene, or hexafluoropropylene.

Consequently, following the above-described plasma activation of the pre-coated stent, the stent remains in the plasma chamber, VDF is introduced at a flow rate of about 60 sccm and a pressure of above 80 mTorr, for example, between about 80 mTorr and about 100 mTorr, and argon plasma is re-initiated by applying the RF power of about 60 W to cause the formation of PVDF-like coating which serves as a bulk of the topcoat membrane. The time needed for plasma-induced polymerization can be between about 2 to 15 minutes. The plasma is then turned off by terminating the RF power.

A RF energy source is used to generate plasma. The power of the plasma field can be maintained at a power/flow function of between about 20 to 100 MJ/Kg. Process parameters for the argon plasma that can be employed are listed in Table 3 below.

TABLE 3

The Parameters of the Plasma Used for Polymerization

| Parameter | Parameter Range | Exemplary Value |
|---|---|---|
| Gas flow rate (sccm) | 10 to 1,000 | 100 |
| Volume of chamber (cm$^3$) | — | 2,000 |
| Monomer flow rate (sccm) | 10 to 300 | 60 |
| Monomer pressure (mTorr) | 80 to 100 | 90 |
| RF power (Watts) | 5 to 1,000 | 60 |
| RF frequency (kHz) | 0.2 to 2,800 | 13.56 |
| Bias voltage--stent (kV) | 0 to −10 | −5 |
| Pulse width--stent (μs) | 7 to 20 | 20 |
| Bias voltage--grid in the PIIU (kV) | 0 to −10 | −5 |
| Time of exposure of VDF (min) | 2 to 15 | 7.5 |

After the bulk sub-layer of the topcoat membrane based on the PVDF-like polymer has been formed as described above, a thin surface sub-layer of the topcoat membrane is made. To fabricate the surface sub-layer of the topcoat membrane, the pressure of VDF in the plasma chamber is gradually reduced to below about 30 mTorr, for example, between about 20 mTorr and about 30 mTorr, while the flow rate of VDF remains the same. The plasma is maintained for about 3 minutes after the desirable lower pressure has been reached to cause polymerization of VDF and formation of a surface PE-like sub-layer of the topcoat membrane. This layer can have a thickness of about 200 nanometers. Process parameters (except for the monomer pressure), including the parameters for the argon plasma that can be employed, are the same as those listed in Table 3.

As a result of the above-described process, the pre-coated stent is coated with a topcoat membrane, the membrane comprising a PVDF-rich bulk sub-layer having good diffusion characteristics for hydrophilic biological agents, and a PE-like biologically inert surface sub-layer. The total thickness of the topcoat membrane can be between about 100 and 500 m. The RF power is then switched off and the plasma chamber purged with argon to allow for the recombination of any residual free radicals.

According to another embodiment of the present invention, the stent can be further modified by grafting an agent having specific biological properties to the outer surface of the topcoat membrane. To graft such an agent, a compound carrying a reactive functionality is first bonded the topcoat membrane fabricated as described above.

To bond the reactive compound, the stent coated with the membrane is kept in the plasma chamber and the reactive compound, for example, an unsaturated carboxylic acid, such as acrylic acid having the formula $CH_2=CH-COOH$ is introduced into the plasma chamber in a gaseous form. Carbon dioxide can be added to acrylic acid to control the properties of the resulting polymer. The amount of carbon dioxide being added can be determined by those having ordinary skill in the art and is dependent on factors such as the end properties of the resulting polymer that are desired. Besides acrylic acid, other unsaturated carboxylic acids or blends thereof can be used in the alternative, e.g., methacrylic acid having the formula $CH_2=C(CH_3)-COOH$, or maleic acid having the formula $HOOC-CH=CH-COOH$. Unsaturated amines, for example, allylamine, having the formula $CH_2=CH-CH_2-NH_2$ can be also used as reactive compounds.

Plasma field is then created by applying an RF power of between about 80 and 120 W to the stream of acrylic acid or acrylic acid/carbon dioxide to cause bonding of acrylic acid to the topcoat membrane to form a coupling layer. The time needed for such plasma-induced formation of the coupling layer can be between about 2 to 15 minutes. The plasma is then turned off by terminating the RF power, the pressure is reduced to below about 1 mTorr, and the chamber is flooded with argon gas.

As a result of the above-described bonding process, the outer surface of the topcoat membrane becomes enriched with carboxyl groups being present in the coupling layer (amino groups are present if allylamine is used for forming the coupling layer). A compound having desired biological properties can be chemically conjugated to the coupling layer by utilizing the coupling layer's carboxyl groups (or amino groups if allylamine is used for forming the coupling layer). One example of such compound can be poly(ethylene glycol) (PEG) having the formula $HO-[CH_2-CH_2-O]_n-H$. PEG possesses a high degree of biological inertness, and consequently the topcoat membrane, having PEG bonded to it, will have improved compatibility with body fluids with which the topcoat comes in contact.

Other examples of compounds that can be used include superoxide dismutate-mimetics (SOD-mimetics or SODm) or an adduct of PEG with SODm (PEG-SODm). SOD-mimetics are oxidoreductases-based complexes that contain cations of copper, iron, or manganese. SOD-mimetics are major intracellular enzymes that protects the cell against oxygen toxicity by dismutating the radical oxygen superoxide, $O_2^-$, to oxygen and hydrogen peroxide. Thus, SODm or PEG-SODm adducts have anti-inflammatory properties, and the topcoat membrane having SODm or a PEG-SODm adduct bonded to it will have improved anti-inflammatory effect.

PEG's functionalized derivatives that can be also conjugated to the topcoat membrane via the coupling layer. Representative examples of such derivatives include PEG-isocyanate, PEG-epoxide, amino-terminated PEG (PEG-$NH_2$), and an amino derivative of PEG-SODm (PEG-$NH_2$—SODm). Other examples of biologically active substances that can be used for conjugation include diazenium diolate type nitric oxide donors and polysaccharides such as hyaluronic acid or heparin and derivatives and analogs thereof.

One way of bonding of PEG or PEG-SODm to the topcoat membrane can be by direct esterification of the surface carboxyl groups which are present in the coupling layer with terminal hydroxyl groups of PEG or PEG-SODm. The reaction may need to be catalyzed by a suitable catalyst. PEG can be in an oligomeric or polymeric form and can have a molecular weight within a range of between about 500 and about 30,000 Daltons. Alternatively, if allylamine is used for making the coupling layer, the surface amino groups can be directly alkylated by PEG or PEG-SODm. Those having ordinary skill in the art can determine the conditions under which the reaction of direct esterification or alkylation can be conducted.

If PEG-$NH_2$ or PEG-$NH_2$—SODm is used for conjugation, instead of direct esterification or alkylation described above, amino groups pendant on the PEG molecule can be used for bonding to the carboxyl groups of the coupling layer, as described in detail below. Alternatively, if allylamine is used for making the coupling layer, a carboxyl derivative of PEG or PEG-SODm (PEG-COOH or PEG-COOH—SODm, respectively) can be used for bonding to the amino groups of the coupling layer.

According to yet another embodiment of the present invention, the stent can be modified by applying a finishing coat comprising a biologically compatible polymer over the topcoat membrane. One example of such biologically compatible polymer can be EVAL. Those having ordinary skill in the art can select another biologically compatible polymer, or a blend of more than one of such polymers, if desired. To make a stent comprising the finishing coat of the biologically compatible polymer, the topcoat membrane is made as described above and an intermediate layer can be formed on the topcoat membrane. The intermediate layer can be obtained by plasma polymerization of an unsaturated carboxylic acid, such as acrylic acid or, alternatively, methacrylic or maleic acid. The above-described procedure for plasma polymerization of acrylic acid can be used.

EVAL can then be dissolved in a suitable solvent and the solution can be applied onto the intermediate layer by any common method to form the finishing layer. As a result of the presence of the carboxyl groups in the intermediate layer, adhesion of EVAL to the outermost layer of the topcoat membrane leading is improved.

EVAL is only one example of a polymer that can be used to fabricate the drug reservoir layer and/or the optional finishing layer. Representative examples of other polymers that can be used include poly(hydroxyvalerate), poly(hydroxybutyrate-co-valerate), polydioxanone, polyorthoester, polyanhydride, cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers (such as polyvinyl methyl ether), polyvinylidene halides, such as polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The invention has been disclosed with reference to a stent, such as balloon expandable or self-expandable stents. However, other implantable medical devices are also within the scope of the invention. Examples of such implantable devices include stent-grafts, grafts (e.g., aortic grafts), artificial heart valves, abdominal aortic aneurysm devices, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Examples of therapeutic substances that can be used include substances which can inhibit the activity of vascular smooth muscle cells. More specifically, the substance can be aimed at inhibiting abnormal or inappropriate migration and/or proliferation of smooth muscle cells for the inhibition of restenosis. The substance can also include any substance capable of exerting a therapeutic or prophylactic effect in the practice of the present invention. For example, the substance can be for enhancing wound healing in a vascular site or improving the structural and elastic properties of the vascular site. Examples of therapeutic substances include antiproliferative substances such as derivatives and analogs of actinomycin D (manufactured by Sigma-Aldrich of Milwaukee, Wis.), or COSMEGEN available from Merck & Co. Inc. of Whitehouse Station, N.J. Synonyms of actinomycin D include dactinomycin, actinomycin IV, actinomycin $I_1$, actinomycin $X_1$, and actinomycin $C_1$. The therapeutic substance can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S. A. of Frankfurt, Germany) methotrexate, azathioprine, vincristine, vinblastine, fluorouracil, doxorubicin hydrochloride (e.g. Adriamycin® from Pharmacia & Upjohn, of Peapack N.J.), and mitomycin (e.g. Mutamycin® from Bristol-Myers Squibb Co. of Stamford). Examples of such antiplatelets, anticoagulants, antifibrin, and antithrombins include sodium heparin, low molecular weight heparins, heparinoids, heparin derivatives having hydrophobic counter ions, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax made by Biogen, Inc., of Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co. of Stamford), cilazapril or lisinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., of Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, 40-O-tetrazole-rapamycin; tacrolimus and dexamethasone.

The embodiments of the present invention are illustrated by the following examples.

EXAMPLE 1

A stent coated with EVAL is activated by being subjected to treatment by argon plasma. The parameters of the plasma are provided in Table 1. As a result of the plasma treatment, free radicals and peroxides are formed on the EVAL surface.

VDF is introduced at a flow rate of about 60 sccm and a pressure of about 90 mTorr, and argon plasma is re-initiated by applying the RF power of about 60 W to cause the formation of PVDF-like coating which serves as a bulk of the topcoat membrane. Other parameters of the argon plasma used at this time are provided in Table 3. The time needed for plasma-induced polymerization is about 4 minutes. The plasma is then turned off by terminating the RF power. The resulting PVDF-like polymer layer can have thickness of about 125 nanometers.

Alternatively, instead of the continuous wave plasma, a pulsed RF-plasma, for example, the RF-plasma having a duty cycle in a range of between 10% and 100% can be used to induce plasma polymerization of VDF. The parameters of the 35% and 25% pulsed plasma are provided in Tables 4 and 5, respectively.

TABLE 4

The Parameters of the 35% Pulsed Plasma Used for Polymerization of Vinylidene Fluoride

| Value | Power (W) | Flow Rate (sccm) | Pressure (mTorr) | Time (min) | Duty Period (%) | Frequency (kHz) | Average Power (W) |
|---|---|---|---|---|---|---|---|
| Range | 5–450 | 30–200 | 80–120 | 2–10 | 35 | Continuous to 6.0 | 50–120 |
| Exemplary value | 190 | 60 | 90 | 4 | 35 | 4.0 | 60 |

TABLE 5

The Parameters of the 25% Pulsed Plasma Used for Polymerization of Vinylidene Fluoride (Exemplary Values)

| Power (W) | Flow Rate (sccm) | Pressure (mTorr) | Time (min) | Duty Period (%) | Frequency (kHz) |
|---|---|---|---|---|---|
| 280 | 60 | 90 | 4 | 25 | 3.5 |

The pressure of VDF in the plasma chamber is then slowly reduced to about 20 mTorr while maintaining the flow rate of VDF at about 60 sccm. The pressure is maintained for about 3 minutes. Either continuous wave plasma or pulsed plasma can be used. Plasma causes polymerization of VDF and formation of a surface PE-like sub-layer of the topcoat membrane.

This layer can have a thickness of about 200 nanometers.

After about 3 minutes, the RF power is turned off and the plasma chamber is purged with argon to allow for the recombination of residual free radicals. The conditions under which the process can be conducted (other than the monomer pressure), including the parameters of the plasma, are provided in Table 3 (for continuous wave plasma) and in Tables 4–5 (for pulsed plasma). As a result, a topcoat membrane can be formed on the stent, the membrane including a PVDF-rich bulk, and a PE-like biologically inert surface sub-layer.

EXAMPLE 2

A stent coated with EVAL is activated by being subjected to treatment by argon plasma as described in Example 1. A topcoat membrane comprising a PVDF-like bulk and a PE-like surface sub-layer is plasma-deposited on the stent as described in Example 1. The PE-like surface sub-layer is then further modified. Before the plasma chamber is argon-purged, the pressure is reduced to about 1 mTorr, and streams of acrylic acid gas and of carbon dioxide are introduced to the plasma chamber. Acrylic acid is introduced at a rate of about 4 mmol/min (0.2 sccm), and carbon dioxide—at a rate of about 90 sccm. Acrylic acid/carbon dioxide plasma is initiated by applying RF power of between about 80 W and 100 W, for example, about 90 W. The plasma is maintained for about 3 minutes and then discontinued by turning off the RF power. The chamber is then pumped down to less than about 1 mTorr of pressure and flooded with argon for 3 minutes.

As a result of the above-described process, a coupling layer is formed on the PE-like surface of the topcoat membrane. The coupling layer contains carboxyl groups which is achieved by bonding acrylic acid to the PE-like structure. Overall, the structure is formed on the surface of the topcoat membrane where the acrylic acid-derived units are built-in the quasi-PE backbone. This structure can be schematically represented as Z—COOH, where —COOH is the carboxyl group provided by acrylic acid, and Z is —[$CH_2$—$CH_2$X]$_n$—, where X is the —CH—$CH_2$ group provided by acrylic acid. The carboxyl groups are pendant on the tertiary carbons in X.

The carboxylated structure Z—COOH is then used for conjugating PEG, a highly biologically compatible product. Due to the presence of hydroxyl groups, PEG is capable of entering reactions of esterification with carboxylated surface of the topcoat membrane, as shown by reaction (III):

$$Z\text{—COOH} + \text{HO—}[CH_2\text{—}CH_2\text{—O}]_n\text{—H} \rightarrow Z\text{COO—}[CH_2\text{—}CH_2\text{—O}]_n\text{—H} \quad \text{(III)}$$

The reaction of direct esterification (III), can be carried in the presence of 1,3-dicyclohexylcarbodiimide (DCC) or 4-dimethylaminopyridine (DMAP). DCC activates the carboxyl group in Z—COOH, thus facilitating the esterification reaction of nucleophilic substitution (III).

Reaction (III) is conducted under standard conditions known to those having ordinary skill in the art of chemistry. An insoluble substance, N,N-dicyclohexylurea is a by-product of the reaction (III). PEG can be in an oligomeric or polymeric form and can have a molecular weight within a range of between about 500 and about 30,000 Daltons. Thus, PEG is bonded to the topcoat membrane providing the stent coating with an enhanced long-term biocompatibility.

EXAMPLE 3

A PVDF-like/PE-like topcoat membrane is deposited on a stent as described in Example 1. The surface PE-like sublayer is modified as described in Example 2 and the carboxylated structure Z—COOH is formed. The carboxylated structure Z—COOH is then used for conjugating poly (ethylene glycol)-isocyanate adduct (PEG-ISO). PEG-ISO is a PEG based product having isocyanate fragments —N=C=O. An example of a PEG-ISO suitable for bonding to the topcoat membrane is a methoxylated PEG-ISO adduct $CH_3—[O—CH_2—CH_2]_n—N=C=O$. This adduct, manufactured by Shearwater Corp. of Huntsville, Ala., has a molecular weight of about 5,000 which corresponds to the value of the integer "n" of about 112.

Due to the presence of the isocyanate groups, PEG-ISO is chemically very active and can react with carboxyl group of Z—COOH via the —N=C=O group of PEG-ISO, having strong electron accepting properties, as illustrated by reaction scheme (IV):

Since Z—COOH is a relatively weak nucleophilic agent, reaction (IV) will be facilitated in the presence of suitable catalysts, for example, tertiary amines such as triethylamine or triethylenediamine, or organo-tin compounds, such as tin dibutylacetate or tin tributylacetate. The condition under which reaction scheme (IV) is conducted can be determined by those having ordinary skill in the art. As a result, the biologically compatible PEG-ISO is firmly bonded to the topcoat membrane to form the urethane product of reaction (IV). Thus, the stent coating will include the topcoat membrane with an enhanced long-term biocompatibility.

EXAMPLE 4

A PVDF-like/PE-like topcoat membrane is deposited on a stent as described in Example 1. The surface PE-like sublayer is modified as described in Example 2 and the carboxylated structure Z—COOH is formed. The carboxylated structure Z—COOH is then used for conjugating poly (ethylene glycol)-epoxide adduct (PEG-EPO). PEG-EPO is a PEG-based product having epoxy fragments An example of a PEG-EPO suitable as a modifier for EVAL is a methoxylated PEG-EPO adduct, methoxy-PEG-glycidyl ether, having a general formula The adduct, manufactured by Shearwater Corp., like PEG-ISO, has a molecular weight of about 5,000 which corresponds to the value of the integer "n" of about 112.

Epoxy groups in PEG-EPO are reactive, and PEG-EPO can react with carboxyl group of Z—COOH via the nucleophilic substitution $S_N2$ reaction of the epoxy group of PEG-EPO. Normally, the proton of the carboxyl group attacks the less substituted α-carbon atom of the oxyran ring of the epoxy group. The β-carbon is less accessible due to the steric hindrances. As the result of the proton attack on the α-carbon atom, the ring opens and PEG-EPO can be bonded as shown by reaction scheme (V):

Reaction (V) is generally slow; it can be accelerated in the presence of optional electron acceptors, in order to facilitate electrophilic polarization of the C—O bond of the epoxy ring, thus making the subsequent attack by the proton of the carboxyl group of Z—COOH easier.

Accordingly, bonding of PEG-EPO is facilitated in the presence of electrophilic ring-opening catalysts, for instance, aprotonic acids such as amine-boron trifluoride adducts or tertiary amines. The condition under which this reaction is conducted can be determined by one having ordinary skill in the art. As a result, the biologically compatible PEG-EPO is firmly bonded to the topcoat membrane. Thus, the stent coating will include the topcoat membrane with an enhanced long-term biocompatibility.

EXAMPLE 5

A PVDF-like/PE-like topcoat membrane is deposited on a stent as described in Example 1. The surface PE-like sublayer is modified as described in Example 2 and the carboxylated structure Z—COOH is formed. The carboxylated structure Z—COOH is then used for conjugating with $PEG-NH_2$.

Due to the presence of the amino groups, $PEG-NH_2$ is chemically active and can be acylated by the carboxyl groups of Z—COOH. Accordingly, Z—COOH reacts with $PEG-NH_2$. The reaction is carried in the presence of ethyl-3(3-dimethylaminopropyl) carbodiimide, also known as carbodiimide or EDC, having the formula $CH_3—CH_2—N=C=N—CH_2—CH_2—CH_2—N(CH_3)_2$. EDC is manufactured by Pierce Corp. of Rockford, Ill. DCC can be also used instead of EDC.

Z—COOH reacts with EDC and forms an O-acylisourea, an amine-reactive intermediate. This intermediate is unstable in aqueous environment and immediately reacts with $PEG-NH_2$ utilizing $PEG-NH_2$'s amino groups. The path of the reaction is via the nucleophilic attack of the carbon of the carboxyl group of Z—COOH by the electron-rich nitrogen of the amino group of $PEG-NH_2$, followed by the formation of the peptide bond —NH—CO—. Water is the by-product. The process is schematically shown by the acylation reaction scheme (VI):

Reaction scheme (VI) shows only the final products of the process. The intermediate stage of the formation of O-acylisourea is omitted. The condition under which reaction scheme (IV) is conducted can be determined by those having ordinary skill in the art. As a result, the biologically compatible PEG-NH$_2$ is firmly bonded to the topcoat membrane to form the peptide product of reaction (IV). Thus, the stent coating will include the topcoat membrane with an enhanced long-term biocompatibility.

EXAMPLE 6

A PVDF-like/PE-like topcoat membrane is deposited on a stent as described in Example 1. The surface PE-like sub-layer is modified as described in Example 2 and the carboxylated structure Z—COOH is formed. The carboxylated structure Z—COOH is then used for conjugating with SODm. Manganese-based SODm, manganese(II)dichloro-aminoethylthiolated pentaazatetracyclohexacosatriene (SOD-40470) manufactured by Metaphore Pharmaceuticals, Inc., St. Louis, Mo. is one example of SODm that can be used first to form an adduct with PEG followed by bonding this adduct to the topcoat membrane. This complex seven-ligand SODm has a formula where R is 2-aminoethylmercapto group, —SCH$_2$CH$_2$NH$_2$. Those having ordinary skill in the art can also select other types of SODm.

Due to the presence of the primary amino ligands, SOD-40470 is chemically active and can react with Z—COOH. Just as in the case of modification with PEG-NH$_2$, the reaction is carried in the presence of EDC or DCC. The mechanism of the reaction is via acylation of the amino group of SOD-40470 and is similar to reaction scheme (VI). Other SOD-mimetics can be used so long as they have amino groups. The conditions under which this reaction is conducted can be determined by one having ordinary skill in the art. As a result, the biologically compatible amino ligand-containing SOD-40470 can be firmly bonded to the topcoat membrane to form the peptide-type adduct. Thus, the stent coating will include the topcoat membrane with an enhanced long-term biocompatibility.

As a variation of Example 6, SOD-40470 can be first conjugated to PEG, and the PEG-SODm adduct can be then conjugated to the topcoat membrane as described above. Instead of pure PEG, PEG-NH$_2$ can be used for forming an adduct with SOD-40470. As a result, the product including both SODm and PEG can be firmly bonded to the topcoat membrane to form the peptide-type adduct to provide the topcoat membrane with even more enhanced long-term biocompatibility.

EXAMPLE 7

A PVDF-like/PE-like topcoat membrane is deposited on a stent as described in Example 1. The surface PE-like sub-layer is modified as described in Example 2 and the carboxylated structure Z—COOH is formed.

A solution containing between about 0.1 and about 15 mass % of EVAL and the balance of dimethylacetamide solvent is prepared. The solution is applied by spraying or dipping onto the topcoat membrane and dried. As a result, an EVAL layer is formed over the carboxylated structure Z—COOH, the carboxyl groups enhancing the adhesion of the EVAL layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of forming a coating for an implantable medical device, the method comprising:
   (a) exposing the device to polyvinylidene fluoride in gaseous form at an initial pressure above about 80 mTorr;
   (b) initiating a plasma to cause the decomposition/recombination of the vinylidene fluoride to form a polymeric bulk layer of the coating; and
   (c) changing the initial pressure of the vinylidene fluoride to a final pressure below about 30 mTorr while maintaining the plasma to form a polymeric surface layer of the coating, wherein the polymer of the bulk layer and the polymer of the surface layer of the coating comprise different polymers.

2. The method of claim 1, wherein the implantable medical device is a radially expandable stent.

3. The method of claim 1, wherein the medical device includes a polymer layer formed thereon, and wherein the method additionally comprises plasma activating the surface of the polymer layer prior to exposing the device to the vinylidene fluoride.

4. The method of claim 3, wherein the polymer layer is made from a polymer comprising poly(ethylene-co-vinyl alcohol) or poly(tetrafluoro ethylene).

5. The method of claim 3, wherein the plasma activation is conducted by an argon plasma or a mixture of an argon and oxygen plasma.

6. The method of claim 1, wherein the initial pressure is between about 80 mTorr and about 100 mTorr.

7. The method of claim 1, wherein the final pressure is between about 20 mTorr and about 30 mTorr.

8. The method of claim 1, further comprising forming a coupling layer on the surface layer of the coating and applying a biologically compatible substance to the surface layer.

9. The method of claim 8, wherein the coupling layer is formed by exposing the surface layer of the coating to a reactive unsaturated compound and initiating a plasma to cause the polymerization of the reactive unsubstituted compound.

10. The method of claim 9, wherein the biologically compatible substance is applied by grafting the substance to the coupling layer.

11. The method of claim 9, wherein the reactive unsaturated compound is selected from a group consisting of acrylic acid, methacrylic acid, maleic acid and allylamine.

12. The method of claim 8, wherein the biologically compatible substance is selected from poly(ethylene glycol), superoxide dismutate-mimetics, diazenium diolate type nitric oxide donors, polysaccharides and derivatives or analogs thereof.

* * * * *